(12) United States Patent
Matsumoto

(10) Patent No.: US 6,783,240 B2
(45) Date of Patent: Aug. 31, 2004

(54) COMPUTER CONTROLLED PERIMETRY SYSTEM

(75) Inventor: Yoshihiro Matsumoto, Toda (JP)

(73) Assignee: Inami & Co., Ltd., Tokyo (JP)

( * ) Notice: Subject to any disclaimer, the term of this patent is extended or adjusted under 35 U.S.C. 154(b) by 0 days.

(21) Appl. No.: 10/267,755

(22) Filed: Oct. 10, 2002

(65) Prior Publication Data

US 2004/0070731 A1 Apr. 15, 2004

(51) Int. Cl.$^7$ .............................................. A61B 3/02
(52) U.S. Cl. ................................................. 351/225
(58) Field of Search ............................. 351/224, 225, 351/226; 359/227, 234, 235, 236

(56) References Cited

U.S. PATENT DOCUMENTS

| | | | | |
|---|---|---|---|---|
| 2,441,031 A | * | 5/1948 | Papritz | 351/226 |
| 4,255,022 A | * | 3/1981 | Kuether et al. | 351/226 |
| 5,108,170 A | * | 4/1992 | Sugiyama | 351/226 |
| 5,459,536 A | | 10/1995 | Shalon et al. | |
| 5,870,169 A | | 2/1999 | Koest | |
| 6,318,860 B1 | * | 11/2001 | Suzumura | 351/224 |

FOREIGN PATENT DOCUMENTS

| | | |
|---|---|---|
| EP | 0 659 382 A2 | 6/1995 |
| EP | 1 236 432 A2 | 9/2002 |

* cited by examiner

Primary Examiner—George Manuel
(74) Attorney, Agent, or Firm—Oblon, Spivak, McClelland, Maier & Neustadt, P.C.

(57) ABSTRACT

A computer controlled perimetry system, which is easily operated even by an unskilled operator, for accurately measuring a visual field, and with which many patients can be effectively examined, has a dome having a hemispherical inner surface; a projector projecting a light spot onto the inner surface of the dome; an arm for horizontally moving the projector so as to trace a semicircle along the surface of a virtual hemisphere opposite to the dome; a first motor for driving the arm; a second motor for changing the projecting direction of the projector; a liquid crystal display for displaying the light spot projected onto the inner surface of the dome; a monitor display for observing a patient; and a computer storing a program for controlling the rotation of the first and second motors. Thus, the light spot projected by the projector can be swept to any point on the inner surface of the dome.

4 Claims, 5 Drawing Sheets

COMPUTER CONTROLLED PERIMETRY SYSTEM

BACKGROUND OF THE INVENTION

1. Field of the Invention

The present invention relates to perimeters for measuring the visual field of a human eye, and more particularly, the present invention relates to a computer controlled perimetry system for accurately measuring the dynamic and/or static visual field of a patient easily and quickly and without requiring skill, and for recording and storing the measured data.

2. Description of the Related Art

Hitherto, a so-called Goldmann perimeter has been widely used for many years as a measuring apparatus for measuring the visual field of a patient, since the visual field serves as an indicator of glaucoma or brain cancer. This perimeter is effectively used for diagnosing glaucoma since it can accurately measure the dynamic and quantitative visual field of one or both eyes of a patient and thus serves to diagnose glaucoma or to keep track of the progress of the glaucoma. Also, the perimeter is used as an important diagnostic apparatus in the fields of neurosurgery as well as ophthalmology, since some brain cancers can be detected at early developments of those by the perimeter because brain disorders cause changes in the visual field.

FIGS. 1 and 2 are front and rear views, respectively, of the Goldmann perimeter. As shown in FIGS. 1 and 2, the Goldmann perimeter has a dome 1 having a hemispherical inner surface, a projector 2 which projects a light spot and sweeps it from any one point A to any other point B on the inner surface of the dome 1 toward the center of the dome 1, an arm 3 for moving the projector 2 so as to horizontally trace a semicircle along the surface of a virtual hemisphere opposite to the dome 1, and a pantograph 4 for changing the direction of the arm 3 and the projecting direction of the projector 2.

It is assumed that a patient has his head immobilized on a headrest 5 disposed in the dome 1, closes one of his eyes, and stares at a hole 6 disposed in the center of the inner surface of the dome 1. In this state, as shown in FIG. 2 illustrating the rear side of the perimeter shown in FIG. 1, while checking the direction of the face, i.e., the direction of the line of sight, of the patient with a telescope 7 disposed on the rear side of the hole 6, a laboratory technician grips a gripper 8 disposed at the end of the pantograph 4 and moves it from one point on a recording chart 9, corresponding to the point A, to another point on the recording chart 9, corresponding to the point B. The recording chart 9 has a similar shape to that of the inner surface of the dome 1. Then, in response to the movement of the gripper 8, a light spot projected from the projector 2 gradually moves from the point A to the point B on the inner surface of the dome 1 with the aid of the pantograph 4, as shown in FIG. 1.

Upon observing the light spot, the patient notifies the laboratory technician by pushing a buzzer 24 in his hand that he has observed the light spot. The laboratory technician records the point B visually identified by the patient on the recording chart 9 with a recording kit provided on the rear side of the gripper 8. By repeating the foregoing projection and sweeping of the light spot along 16 radial lines shown in FIG. 2, the visual field 22 of the patient is recorded on the recording chart 9, as shown in FIG. 2. Such a measurement for obtaining the visual field can be performed for one or both eyes. Since the operation of such a perimeter is well known to those skilled in the art, further description thereof is omitted.

In addition to the above described components, as shown in FIGS. 1 and 2, the perimeter has a chin-rest plate 15 disposed in the headrest 5 for the patient to put his chin thereon, a belt 16 disposed on the headrest 5 for immobilizing the head of the patient, a shaft 17 disposed at the top of the perimeter serving as a rotating axis of the arm 3, a rotating knob 19 disposed at the rear lower part of the perimeter for adjusting the headrest 5, and a light source 20 disposed at the front upper part of the perimeter for illuminating the projector 2.

In order to measure the visual field of a patient with the above described perimeter, a laboratory technician must hold the gripper 8 and accurately move the pantograph 4 and the arm 3 at a fixed projecting rate while checking the posture, i.e., the line of sight, of the patient. Thus, such a perimeter causes a problem in that the number of patients that can be tested per day is limited since the laboratory technician operating the perimeter is required to be highly skilled. Furthermore, the laboratory technician often becomes extremely fatigued. Accordingly, the perimeter is not effectively used for patients even though it has some excellent functions.

SUMMARY OF THE INVENTION

Accordingly, it is an object of the present invention to provide a computer controlled perimetry system, which can be easily and accurately operated even by an unskilled laboratory technician or a doctor, for measuring the visual field of a patient, and also with which a large number of patients can be effectively tested.

The present invention is made to achieve the above-mentioned object. That is, a perimetry system according to the present invention comprises a dome having a hemispherical inner surface; a projector projecting a light spot onto the inner surface of the dome; an arm for horizontally moving the projector so as to trace a semicircle along the surface of a virtual hemisphere opposite to the dome; a first motor for driving the arm; a second motor for changing the projecting direction of the projector; a liquid crystal display for displaying the light spot projected onto the inner surface of the dome; a monitor display for observing a patient; and a computer storing a program for controlling the rotation of the first and second motors. Thus, the light spot projected by the projector can be swept to any point on the inner surface of the dome.

In the perimetry system according to the present invention, the computer for controlling the rotation of the first and second motors may store an additional program by which the arm and the projector move in concert so as to sweep the light spot from one point to another point on the inner surface of the dome, corresponding to the movement of an operator's finger which touches the liquid crystal display.

Furthermore, the perimetry system according to the present invention may further comprise a first controller for controlling the illuminance of the light spot projected onto the inner surface of the dome.

Moreover, the perimetry system according to the present invention may further comprise a second controller for controlling the size of the light spot projected onto the inner surface of the dome.

As described above, the perimetry system according to the present invention can be easily operated even by an unskilled laboratory technician or a doctor, for accurately measuring dynamic and static visual fields of a patient. In addition, a large number of patients can be effectively examined.

DESCRIPTION OF THE PREFERRED EMBODIMENTS

Figure 1:
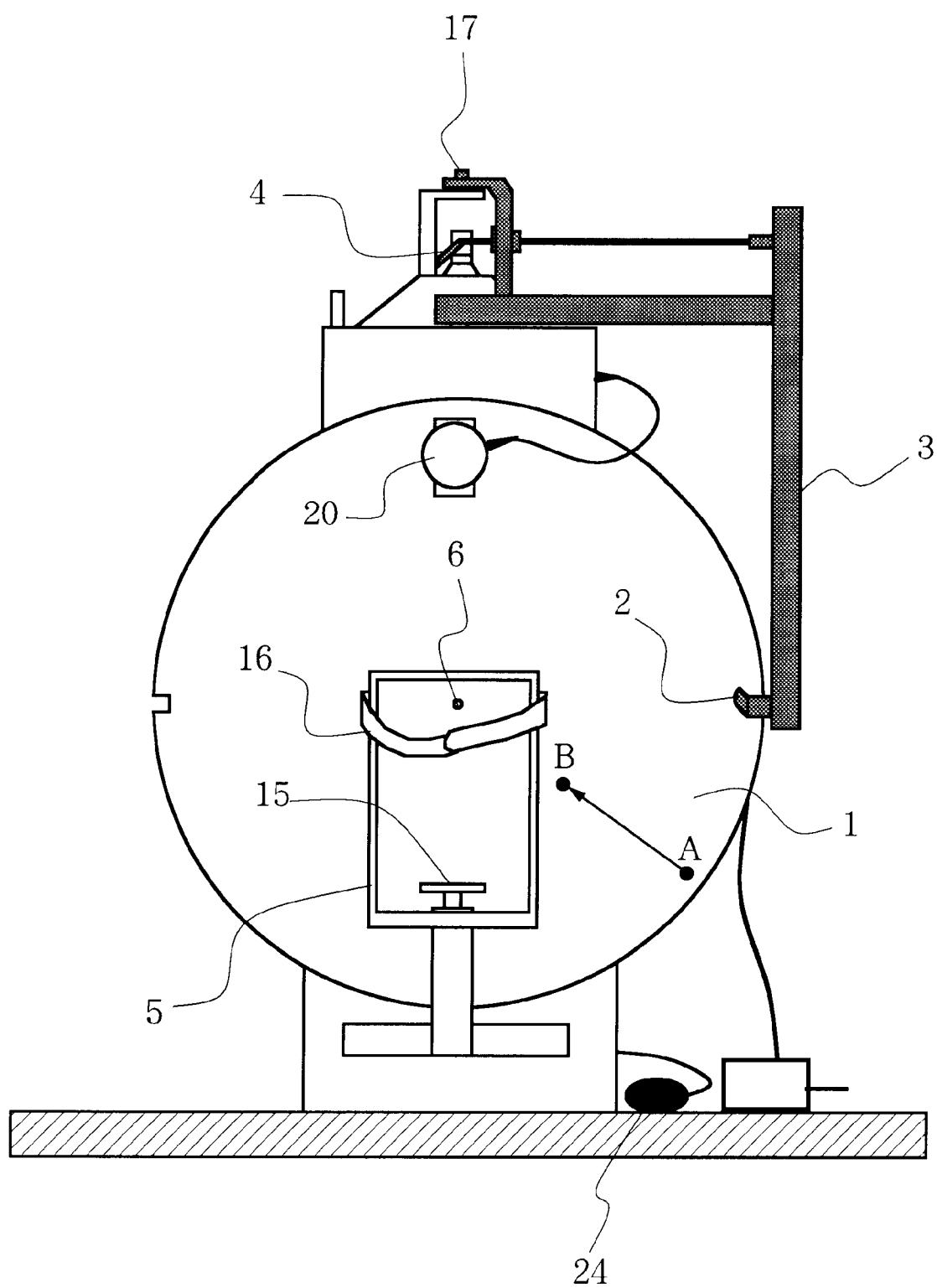
FIG. 1 is a front view of a known perimeter.

Preferred embodiments of the present invention will be described in further detail with reference to the accompanying drawings. Like parts are identified by the same reference numerals as in FIGS. 1 and 2, and a repeated description thereof will be omitted.

Figure 2:
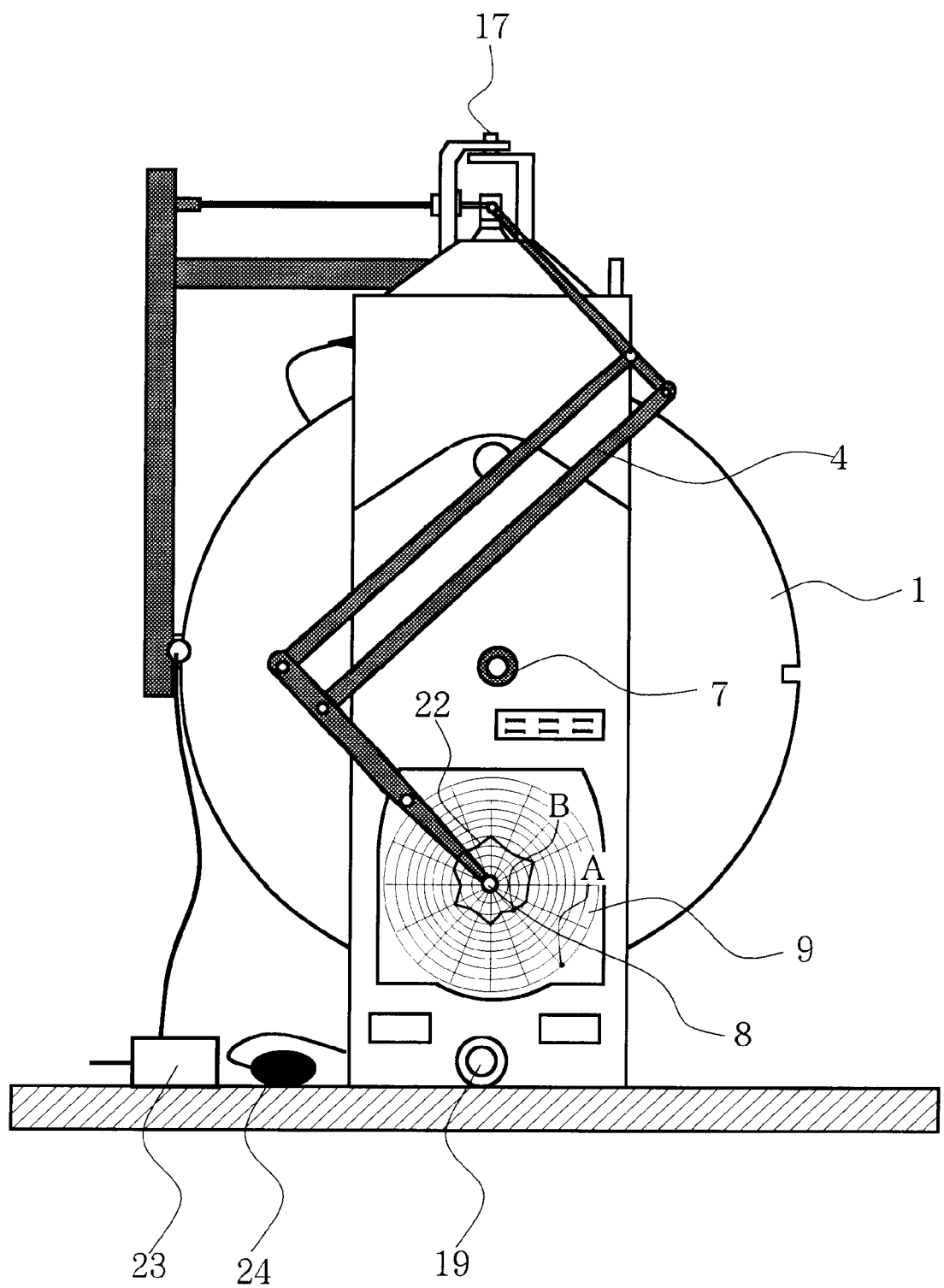
FIG. 2 is a rear view of the known perimeter.
Figure 3:
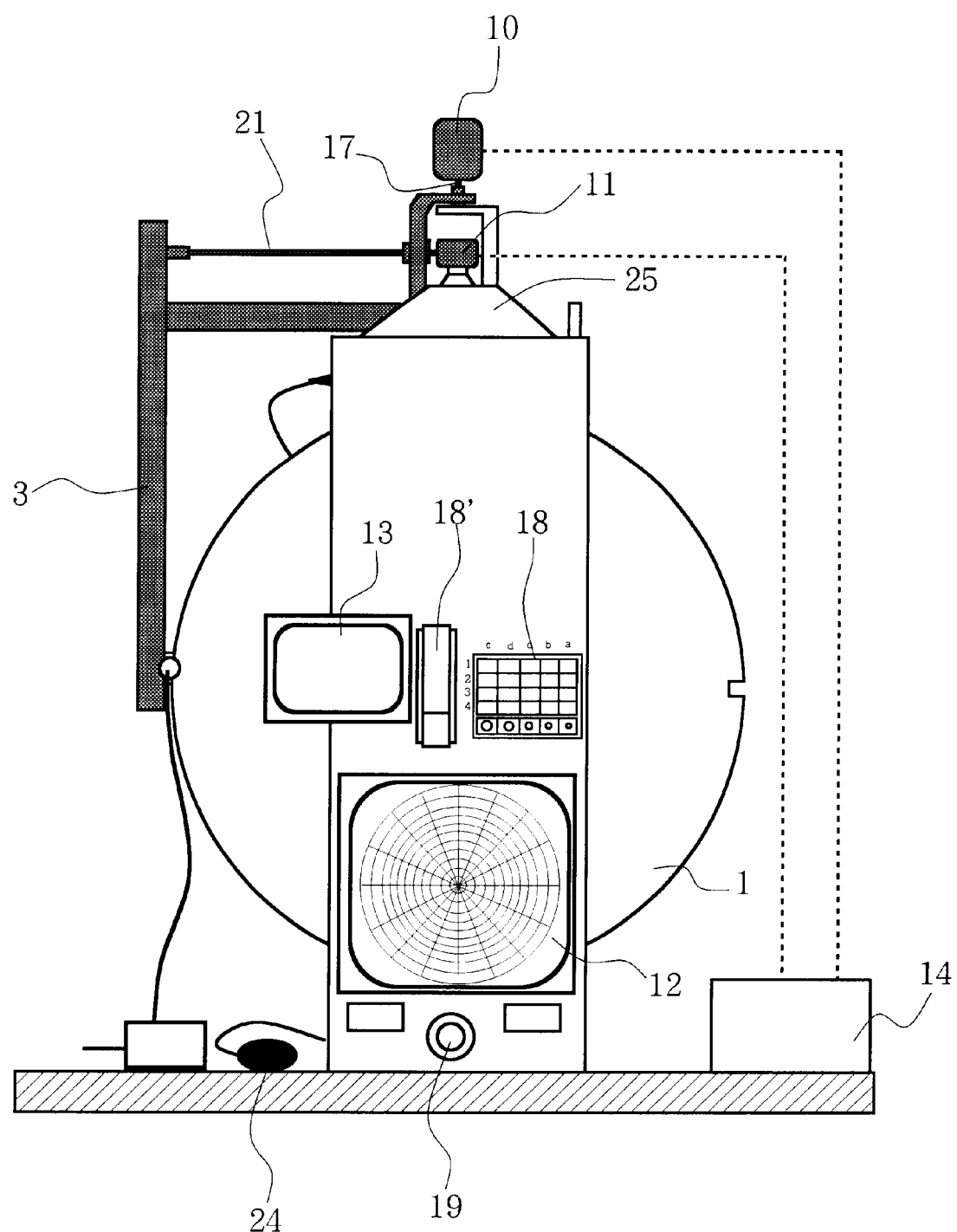
FIG. 3 is a rear view of a perimetry system according to an embodiment of the present invention.

As seen by comparing FIGS. 2 and 3, a computer controlled perimetry system according to an embodiment of the present invention mainly differs from the known Goldmann perimeter shown in FIGS. 1 and 2 with respect to the following three points. First, in place of the pantograph 4 of the known perimeter, the perimetry system of the present invention has first and second motors 10 and 11 for respectively driving the arm 3 and the projector 2 and also has a computer 14 storing a program for controlling the motors 10 and 11 so as to make the arm 3 and the projector 2 move in concert.

Second, in place of the recording chart 9 and the recording kid provided at the end of the gripper 8 of the known perimeter, the perimetry system according to the present invention has a liquid crystal display 12 for automatically displaying a light spot which is projected onto the inner surface of the dome 1 by the projector 2, and for recording and storing the data of the displayed light spot.

Third, in place of the telescope 7 of the known perimeter, the perimetry system according to the present invention has a combination of a CCD camera 18', disposed in the hole 6 lying at the center of the inner surface of the dome 1 shown in FIG. 1, and a liquid crystal monitor display 13 for monitoring the eye movement of a patient. The above-described three points are the major modifications although there are various other minor modifications.

The operation of the perimetry system according to the embodiment of the present invention will now be described. The structure of the front side, which is close to the patient, of the perimetry system is the same as that of the known perimeter shown in FIG. 1.

First, when a patient puts his/her head on the chin-rest plate 15 of the headrest 5 shown in FIG. 1, an operator immobilizes the head of the patient with the belt 16 and then adjusts the headrest 5 by turning the rotating knob 19 so as to properly position the eyes of the patients. Then, the operator instructs the patient to look at the hole 6 lying in the center of the inner surface of the dome 1. According to the conventional art, the operator observes the patient with the telescope 7 disposed at the rear side of the hole 6. On the other hand, according to the present invention, since the CCD camera 18' connected to the liquid crystal display 13 is disposed in the hole 6 in place of the telescope 7, the operator observes the eye or eyes of the patient simply by using the liquid crystal display 13. In other words, the above-described structure allows the operator to very easily observe the eye or eyes of the patient.

Subsequently, the operator switches on the perimetry system while checking that the head of the patient is positioned properly. Then, driven by the first motor 10, the arm 3 rotates horizontally about the shaft 17 at a fixed speed, to behind the head of the patient. The rotating speed can be varied to a desired speed by changing the position of a speed change lever disposed on an operation panel (not shown).

Figure 4:
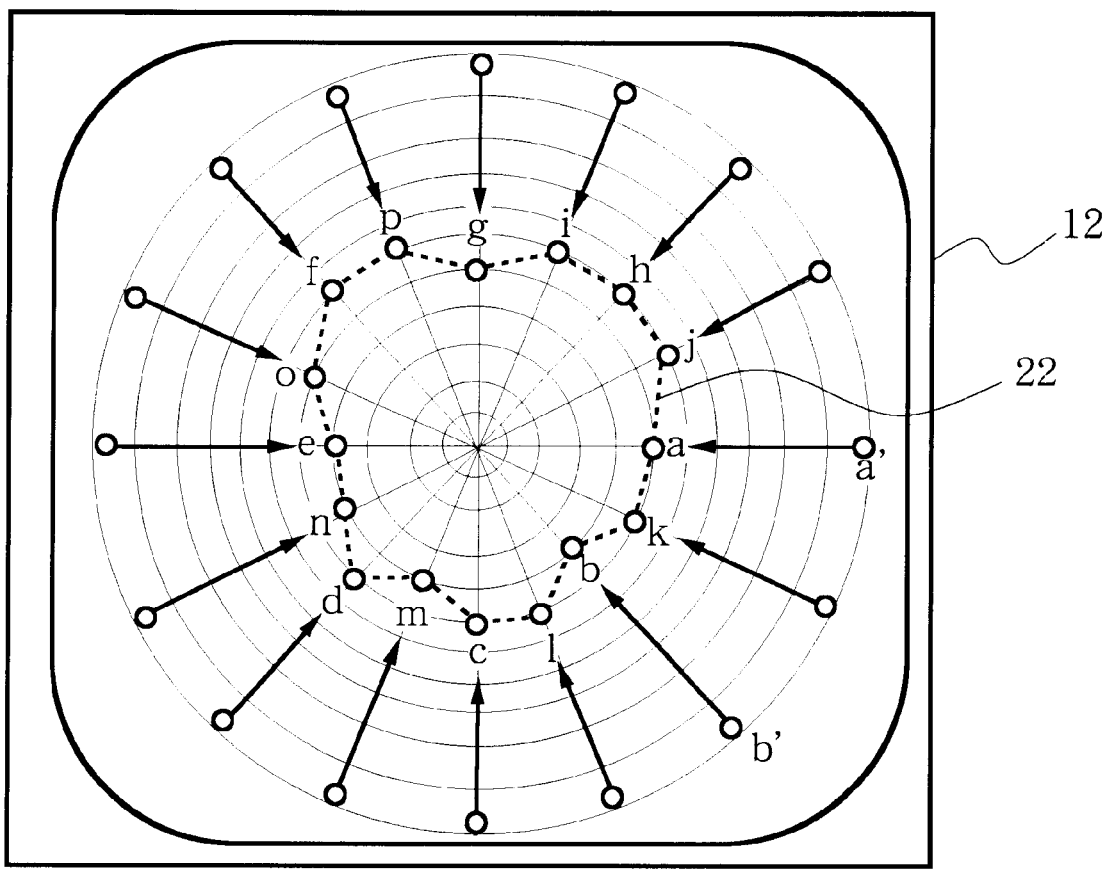
FIG. 4 illustrates a screen of a liquid crystal display of the perimetry system shown in FIG. 3.

When the arm 3 lies behind the head of the patient, the projector 2 changes its direction toward a point A close to the periphery of the inner surface of the dome 1 shown in FIG. 1 and projects a light spot at the point A. Then, the arm 3 rotates at a fixed speed from behind the head of the patient toward the periphery of the dome 1. In concert with the movement of the arm 3, the projector 2 moves at the fixed speed while sweeping a light spot from the point A toward the center of the inner surface of the dome 1. When the patient pushes the buzzer 24 in his/her hand upon observing the light spot, the light spot disappears since light transmitted to the projector 2 from the light source 20 shown in FIG. 1 is shut off. A state in which the patient observes the light spot is correspondingly displayed on the screen of the liquid crystal display 12 shown in FIG. 4. That is, as shown in FIG. 4, a pattern of concentric circles and 16 straight lines, which pass through the center of the circles and are evenly spaced by an angle of 22.5 degrees, are displayed on the screen of the liquid crystal display 12. The above pattern is identical to that drawn on the recording chart 9 in the conventional art. In addition, on the screen of the liquid crystal display 12, a point b' corresponding to the light spot A of the dome 1 is displayed, then the point b' moves along the path indicated by the arrow towards the center, and a point b is displayed in response to a signal generated when the patient pushes the buzzer 24. The number of the straight lines passing through the center can be more than 16 or less than 16.

By sequentially repeating the same operation as described above for the arrow a–a', then the arrow b–b' and so forth, the points a to p are plotted on the screen of the display 12, and, by connecting these points, the visual field 22 (indicated by a dotted line) of the patient is displayed on the screen. The data of the visual field can be printed out and also stored in a computer together with a number identifying a medical record of the patient so as to be read out as required. In addition, the data is available not only in a single perimetry system but also over a plurality of perimetry systems.

The arm 3 is driven to rotate about the shaft 17 by the first motor 10. Although the rotating speed of the arm 3 is fixed while examining a patient, it can be varied to a desired speed as needed using a speed change mechanism on an operation panel (not shown). The projector 2 is disposed near the bottom of the arm 3. Light from the light source 20 shown in FIG. 1 is transmitted to the projector 2 by an optical fiber or the like through the arm 3, and is shut off in response to a signal of the buzzer 24 when pushed by the patient. The inner surface of the dome 1 is illuminated by the light source 20 so as to have a uniform brightness. The perimetry system also has a touch panel 18 for adjusting the brightness of the inner surface and the illuminance of light projected from the projector 2 so that the brightness of the inner surface is set as desired and so that the light spot has a desired size.

In order to change the direction of light projected from the projector 2, the projector 2 is connected to the second motor 11 in a manner such that the rotation of the second motor 11 is transmitted to a rotating shaft 21 disposed between the second motor 11 and the arm 3, then the direction of the rotation is changed at the upper inner portion of the arm 3, and the rotation is transmitted to the projector 2 disposed near the bottom end of the arm 3. The rotating speed of the second motor 11 for changing the projecting direction of the projector 2 is controlled by the computer 14, which stores a program for making the first and second motors 10 and 11 move in concert, so as to project and sweep a light spot, for example, along the direction of each arrow indicated in FIG. 4.

In the perimetry system according to the embodiment of the present invention, when some of the measured data in the visual field measurement shown in FIG. 4 seem suspect due to the improper movement of an eye or eyes by the patient, the operator can reexamine the patient with respect to the suspect data. For example, when the point b is suspect, the operator touches the point b' and another point lying inside the point b on the display 12, and then the visual field with respect to the above suspect point is automatically measured again. That is, the computer 14 for controlling the rotation of the first and second motors 10 and 11 stores a program so that the arm 3 and the projector 2 move in concert so as to sweep the light spot from one point to another point on the inner surface of the dome 1, corresponding the foregoing two touched points on the screen of the display 12.

Figure 5:
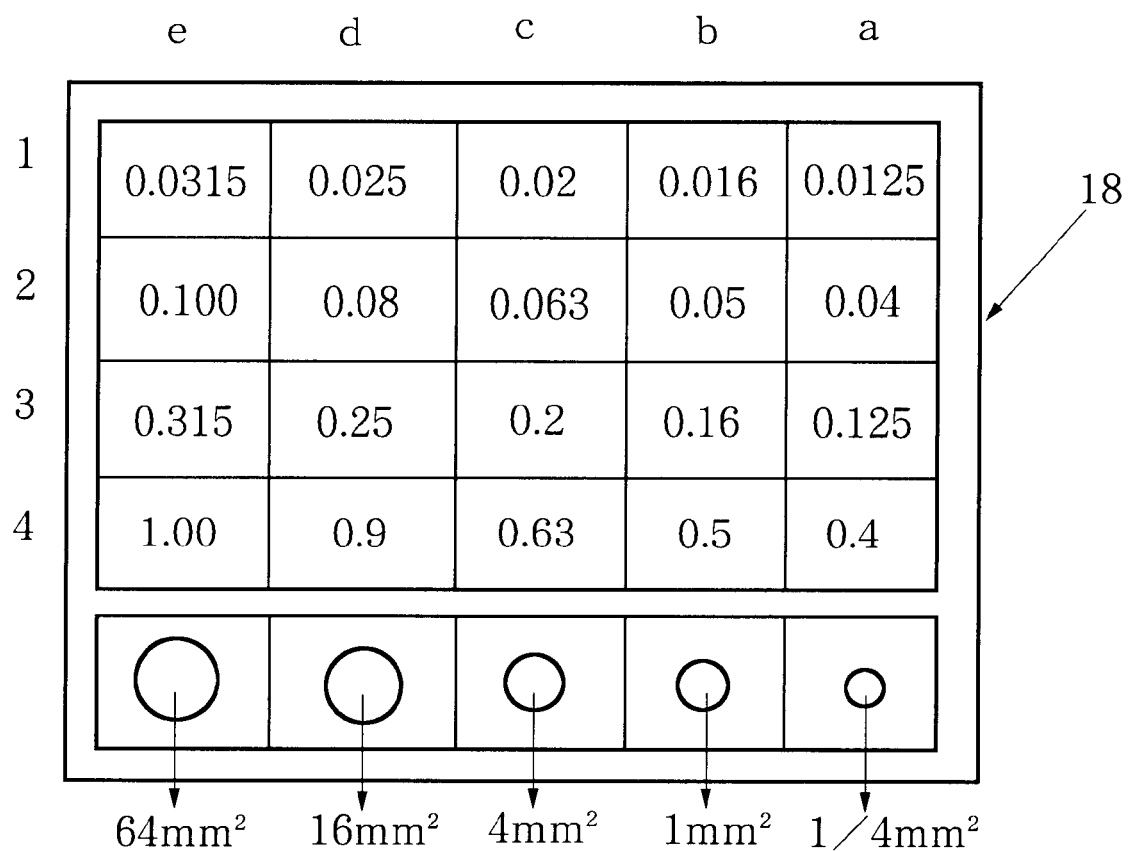
FIG. 5 illustrates a touch panel, for controlling the illuminance and the size of a light spot, of the perimetry system shown in FIG. 3.

Furthermore, the perimetry system according to the embodiment of the present invention preferably has a first controller for controlling the illuminance of the light spot projected onto the inner surface of the dome 1. The first controller includes filters having different transmittances placed in the light path between the light source 20 and the projector 2, for example, in a main part 25 of the perimetry system shown in FIG. 3. Thus, by allowing light from the light source 20 to pass through a single filter or a plurality of filters among the foregoing filters, the first controller varies the illuminance of the light spot projected by the projector 2. Since the touch panel 18 acts as a part of the first controller, the level of the illuminance can be automatically varied by touching segments, which represent different illuminance levels, formed on the touch panel 18, as shown in FIGS. 3 and 5.

In order to automatically vary the illuminance, a group of the foregoing filters having different transmittances are rotated by a small motor so as to be placed in the light path, and, in response to a signal from the touch panel 18, the program of the computer 14 makes the filter or filters change position or makes at least two filters overlap with each other in a manner such that the illuminance of light from the light source 20 decreases. For example, two segments corresponding to e-4 and a-1 represent the maximum illuminance of 100% and the minimum illuminance of 1.25%, respectively, and the other segments represent intermediate illuminance levels between the maximum illuminance and the minimum illuminance, as illustrated in FIG. 5.

Moreover, the periphery system according to the embodiment of the present invention preferably has a second controller for controlling the size of the light spot projected onto the inner surface of the dome 1. The second controller includes a diaphragm mechanism (not shown) disposed in the projector 2 which varies the area of the light spot, for example, in the range from ¼ to 64 mm², as illustrated in FIG. 5. The diaphragm mechanism can be operated manually or automatically. As illustrated in FIG. 5, the touch panel 18 preferably acts as a part of the second controller so that the diaphragm mechanism is automatically controlled by touching the screen of the touch panel 18. In order to automatically vary the area (i.e., the size) of the light spot, the diaphragm mechanism is activated by a small motor in accordance with the control program stored in the computer 14. For example, the touch panel 18 has five segments in the lower field thereof, representing various light spot areas, as illustrated in FIG. 5. By touching a desired segment, the size of the light spot can be automatically varied.

With the above-described method for measuring a visual field by varying the illuminance and the size of a light spot, while increasing the illuminance or the size of a light spot step-by-step, the point at which a patient observes the light spot is determined and data for this point is recorded. As a result, the perimetry system can also measure a static visual field, in addition to a dynamic visual field, which is difficult to measure with known technology.

What is claimed is:

1. A perimetry system comprising:
    a dome comprising a hemispherical inner surface;
    a projector for projecting a light spot onto the inner surface of the dome;
    an arm for horizontally moving the projector so as to trace a semicircle along the surface of a virtual hemisphere opposite to the dome;
    a first motor for driving the arm;
    a second motor for changing the projecting direction of the projector;
    a liquid crystal display for displaying the light spot projected onto the inner surface of the dome;
    a monitor display for observing a patient; and
    a computer storing a program for controlling the rotation of the first and second motors such that the light spot projected by the projector is swept to any point on the inner surface of the dome.

2. The perimetry system according to claim 1, wherein the computer for controlling the rotation of the first and second motors stores an additional program by which the arm and the projector move in concert so as to sweep the light spot from one point to another point on the inner surface of the dome, corresponding to the movement of an operator's finger which touches the liquid crystal display.

3. The perimetry system according to claim 1, further comprising a first controller for controlling the illuminance of the light spot projected onto the inner surface of the dome.

4. The perimetry system according to claim 1, further comprising a second controller for controlling the size of the light spot projected onto the inner surface of the dome.

* * * * *